(12) United States Patent
Squires

(10) Patent No.: US 9,322,197 B2
(45) Date of Patent: Apr. 26, 2016

(54) PRISONER SAFETY SEAT AND METHOD OF USE

(71) Applicant: Keith D. Squires, Morgan, UT (US)

(72) Inventor: Keith D. Squires, Morgan, UT (US)

( * ) Notice: Subject to any disclaimer, the term of this patent is extended or adjusted under 35 U.S.C. 154(b) by 0 days.

(21) Appl. No.: 14/517,748

(22) Filed: Oct. 17, 2014

(65) Prior Publication Data

US 2015/0145311 A1    May 28, 2015

Related U.S. Application Data

(63) Continuation of application No. 13/781,966, filed on Mar. 1, 2013, now abandoned, which is a continuation of application No. 12/612,676, filed on Nov. 5, 2009, now abandoned, which is a continuation-in-part of application No. 11/396,330, filed on Mar. 31, 2006, now Pat. No. 7,712,200, which is a continuation of application No. 10/947,999, filed on Sep. 23, 2004, now abandoned.

(51) Int. Cl.
| | |
|---|---|
| *B23P 11/00* | (2006.01) |
| *B60R 21/00* | (2006.01) |
| *E05B 75/00* | (2006.01) |
| *A47C 7/62* | (2006.01) |
| *B60N 2/24* | (2006.01) |
| *B60R 22/34* | (2006.01) |
| *B60R 99/00* | (2009.01) |
| *A61F 5/37* | (2006.01) |

(52) U.S. Cl.
CPC . *E05B 75/00* (2013.01); *A47C 7/62* (2013.01); *A61F 5/37* (2013.01); *B60N 2/24* (2013.01); *B60R 21/00* (2013.01); *B60R 22/34* (2013.01); *B60R 99/00* (2013.01); *Y10T 29/49904* (2015.01)

(58) Field of Classification Search
CPC ......... E05B 75/00; A61F 5/37; A61F 5/3723; A61F 5/3761; Y10T 29/49904
USPC ......... 29/469; 297/466, 250.1, 254, 474, 475, 297/476, 477, 485, 464, 217.1, 217.3; 280/807; 128/869
See application file for complete search history.

(56) References Cited

U.S. PATENT DOCUMENTS

| | | |
|---|---|---|
| 1,823,697 A | 9/1931 | Nenstiehl |
| 2,150,368 A | 3/1939 | Fitzgerald et al. |
| 2,403,653 A | 7/1946 | Geohegan et al. |
| 2,645,922 A | 7/1953 | Martin |
| 2,701,693 A | 2/1955 | Nordmark et al. |
| 2,830,655 A | 4/1958 | Lalande |
| 2,949,761 A | 8/1960 | Mitchell et al. |
| 3,007,331 A | 11/1961 | Irwin |

(Continued)

FOREIGN PATENT DOCUMENTS

| | | | |
|---|---|---|---|
| EP | 364303 A2 | 4/1990 | |
| GB | 2398824 A | * 9/2004 | ............ B60R 22/46 |

*Primary Examiner* — Essama Omgba
(74) *Attorney, Agent, or Firm* — Snow Christensen & Martineau; Randall B. Bateman; Sarah W. Matthews

(57) ABSTRACT

A prisoner seat security device includes a retractable strap which hooks or clasps onto a prisoner, preferably by a restraint device on the prisoner, such as hand-cuffs. As the prison seats in the seat, the strap retracts. The officer can then lock the retraction mechanism so that the strap will not extend and the prisoner is held in place. When it is desired for the prisoner to get out of the chair, the lock is released, allowing the prisoner to stand the strap to be disconnected.

16 Claims, 9 Drawing Sheets

(56) References Cited

U.S. PATENT DOCUMENTS

| | | | |
|---|---|---|---|
| 3,162,485 A | 12/1964 | Pragnell | |
| 3,281,818 A | 10/1966 | Morgan et al. | |
| 3,321,247 A | 5/1967 | Dillender | |
| 3,385,633 A | 5/1968 | Aizley | |
| 3,554,593 A | 1/1971 | Hawkins | |
| 3,964,029 A | 9/1972 | Noble et al. | |
| 3,992,040 A | 11/1976 | Gannac | |
| 4,173,974 A | 11/1979 | Belliveau | |
| 4,245,856 A | 1/1981 | Ziv | |
| 4,384,427 A * | 5/1983 | Christiansen | 43/26.1 |
| 4,384,735 A | 5/1983 | Maeda et al. | |
| 4,461,493 A | 7/1984 | Doty | |
| 4,467,493 A | 8/1984 | Buchtel | |
| 4,506,912 A | 3/1985 | Ahad | |
| 4,540,218 A | 9/1985 | Thomas | |
| 4,621,835 A | 11/1986 | Edwards | |
| 4,636,276 A * | 1/1987 | Nozaka | 156/353 |
| 4,688,564 A | 8/1987 | Kelly | |
| 4,723,728 A * | 2/1988 | Kanada et al. | 280/807 |
| 4,728,553 A | 3/1988 | Daniels | |
| 4,789,183 A | 12/1988 | Wolfer | |
| 4,874,203 A | 10/1989 | Henley | |
| 4,895,317 A * | 1/1990 | Rumpf et al. | 242/384 |
| 4,898,532 A | 2/1990 | Bercik | |
| 4,925,246 A | 5/1990 | Corcoran | |
| 4,949,679 A | 8/1990 | Wolfer | |
| 4,995,672 A | 2/1991 | Corcoran | |
| 5,050,906 A | 9/1991 | Kneip | |
| 5,074,588 A | 12/1991 | Huspen | |
| 5,261,728 A | 11/1993 | Carmichael | |
| 5,345,947 A | 9/1994 | Fisher | |
| 5,496,092 A | 3/1996 | Williams et al. | |
| 5,511,856 A | 4/1996 | Merrick et al. | |
| 5,538,098 A * | 7/1996 | Sparhawk | 180/270 |
| 5,544,363 A | 8/1996 | McCue et al. | |
| 5,546,962 A | 8/1996 | Power | |
| 5,568,939 A | 10/1996 | Blackburn et al. | |
| 5,581,853 A | 12/1996 | Miller et al. | |
| 5,680,781 A | 10/1997 | Bonds et al. | |
| 5,749,130 A | 5/1998 | Bilyeu et al. | |
| 5,755,235 A | 5/1998 | Magiawala et al. | |
| 5,765,774 A * | 6/1998 | Maekawa et al. | 242/390.9 |
| 5,775,620 A * | 7/1998 | Jabusch et al. | 242/383.1 |
| 5,779,178 A * | 7/1998 | McCarty | 242/384 |
| 5,779,319 A | 7/1998 | Merrick | |
| 5,893,366 A | 4/1999 | Odell et al. | |
| 6,026,661 A | 2/2000 | Spiropoulos | |
| 6,113,325 A | 9/2000 | Craft | |
| 6,138,677 A | 10/2000 | DeVane | |
| 6,267,441 B1 | 7/2001 | Otero | |
| 6,312,056 B1 | 11/2001 | Murphy et al. | |
| 6,334,444 B1 * | 1/2002 | Sisco | 128/869 |
| 6,360,747 B1 | 3/2002 | Velarde et al. | |
| 6,368,262 B1 | 4/2002 | Willoughby et al. | |
| 6,406,230 B1 | 6/2002 | Mason et al. | |
| 6,431,734 B1 | 8/2002 | Curry | |
| 6,655,718 B2 | 12/2003 | Eusebi | |
| 6,676,219 B1 | 1/2004 | Brewer | |
| 6,702,328 B2 | 3/2004 | Malleis et al. | |
| 6,718,894 B2 | 4/2004 | Whaley | |
| 6,725,865 B2 | 4/2004 | Chapman | |
| 6,874,506 B2 | 4/2005 | Chapman | |
| 7,077,475 B2 | 7/2006 | Boyle | |
| 7,137,649 B2 | 11/2006 | Eusebi | |
| 7,140,571 B2 | 11/2006 | Hishon et al. | |
| 7,210,317 B2 | 5/2007 | Beane et al. | |
| 7,340,926 B2 | 3/2008 | Kim et al. | |
| 7,374,494 B2 | 3/2008 | Boyle et al. | |
| 7,481,399 B2 | 1/2009 | Nohren et al. | |
| 7,488,038 B2 | 2/2009 | Boyle et al. | |
| 7,510,246 B2 | 3/2009 | Gruninger | |
| 7,581,416 B1 | 9/2009 | Lenertz | |
| 7,614,689 B2 | 11/2009 | Fowler et al. | |
| 7,712,200 B2 | 5/2010 | Squires et al. | |
| 7,766,422 B2 | 8/2010 | Edwards et al. | |
| 7,770,969 B2 | 8/2010 | Boyle et al. | |
| 7,891,741 B2 | 2/2011 | Lienr, Jr. | |
| 7,922,254 B2 | 4/2011 | Squires et al. | |
| 8,235,463 B2 | 8/2012 | Stiyer et al. | |
| 8,600,622 B2 * | 12/2013 | Kankanala et al. | 701/45 |
| 2001/0001031 A1 | 5/2001 | Craft | |
| 2002/0114679 A1 | 8/2002 | Craft | |
| 2002/0130528 A1 | 9/2002 | Mans | |
| 2003/0042348 A1 | 3/2003 | Salentine et al. | |
| 2003/0042724 A1 | 3/2003 | Eusebi | |
| 2003/0173817 A1 | 9/2003 | Vits et al. | |
| 2003/0217442 A1 | 11/2003 | Peterson | |
| 2004/0005203 A1 | 1/2004 | Craft | |
| 2004/0108707 A1 | 6/2004 | Eusebi | |
| 2006/0061198 A1 | 3/2006 | Squires et al. | |
| 2006/0131457 A1 | 6/2006 | Nohren et al. | |
| 2006/0163963 A1 | 7/2006 | Millard | |
| 2006/0225943 A1 | 10/2006 | Squires et al. | |
| 2006/0270366 A1 * | 11/2006 | Rozenblit et al. | 455/127.1 |
| 2007/0046014 A1 | 3/2007 | Glover et al. | |
| 2007/0063505 A1 | 3/2007 | Eusebi | |
| 2007/0145087 A1 | 6/2007 | Mikesell et al. | |
| 2007/0181079 A1 | 8/2007 | Fong | |
| 2008/0042033 A1 | 2/2008 | Risbara | |
| 2008/0072844 A1 | 3/2008 | Konigsberg | |
| 2008/0168603 A1 | 7/2008 | Ayette et al. | |
| 2008/0289377 A1 | 11/2008 | Alef | |
| 2008/0309062 A1 | 12/2008 | Fowler et al. | |
| 2008/0313862 A1 | 12/2008 | Brekke-Hutchings | |
| 2008/0314336 A1 | 12/2008 | Church et al. | |
| 2009/0102271 A1 | 4/2009 | Squires et al. | |
| 2009/0112408 A1 * | 4/2009 | Kankanala et al. | 701/45 |
| 2010/0117413 A1 | 5/2010 | Squires | |
| 2013/0292978 A1 | 11/2013 | Squires | |

\* cited by examiner

PRISONER SAFETY SEAT AND METHOD OF USE

RELATED APPLICATIONS

The present application is a continuation-in-part of U.S. patent application Ser. No. 11/396,330, filed on Mar. 31, 2006, which is expressly incorporated herein, and which is a continuation of U.S. patent application Ser. No. 10/947,999, filed on Sep. 23, 2004.

BACKGROUND OF THE INVENTION

1. Field of the Invention

The present invention relates to prisoner restraints. More specifically, the present invention relates to restraints which help hold a prisoner in a sitting position.

2. State of the Art

Law enforcement, correction security and military personnel transport handcuffed or otherwise fettered prisoners in various vehicles from one location to another. Traditionally, a police officer arrests a suspect and places him/her in handcuffs. The prisoner is then placed in the police vehicle, which is often equipped with an aftermarket cage that prevents the suspect from moving from the back seat compartment into the front seat compartment. The cage requires hard installation to the vehicle and interferes with the rear passenger compartment being utilized for other purposes.

For a variety of reasons, many officers and departments forego the use of a cage and place the handcuffed prisoner in the front passenger seat and then only use a seatbelt to restrain the prisoner. This practice can allow prisoners to move around freely enough to unlatch the seatbelt, unlock and open the vehicle's door to escape, and in some circumstances to move the handcuffs from behind the back to the front, which facilitates a possible assault on the officer or unlawful operation of the police vehicle.

In addition to moving prisoners in a car or other vehicle, law enforcement officers and other correction officials are required to transition prisoners from different environments. The transition may often require waiting substantial amounts of time. While in the context of a stop in the field this may involve use of a police car, in other cases, the transition may include holding the prisoner for further processing or in preparation for incarceration, questioning, or otherwise receiving the prisoner.

It is very important that during these transitions that the safety of the officers and officials be considered because these transitions have often been very dangerous for the officer. For example, when booking a prisoner, the officer must often enter information about the prisoner. During this time the police officer's attention is drawn away from the prisoner and toward the computer or other system for collecting needed information. During this time the police officer is in at risk that an unruly prisoner may attack the officer. Likewise, there is the risk that the prisoner will attempt to flee while the office is not looking.

On the other hand, it is often dangerous and perhaps illegal to cause a prisoner significant discomfort during this process. A prisoner may be more likely to be passive and cooperative if comfortable. Additionally, a prisoner may be more cooperative if he or she realizes that the chance of escape is minimal.

Thus there is a need for a way to safely and comfortably detain a prisoner that includes features that aid an officer transitioning from detaining the prisoner to the next processing step.

SUMMARY OF THE INVENTION

One application of the present invention incorporates a mounting apparatus which maintains a prisoner in a restrained position while seated to minimize the risk of escape or an assault on an officer.

This may include, for example, an apparatus that hangs over the back of a front passenger side vehicle seat and is fastened to the seat. Towards the bottom of the mounting apparatus may be attached a housing which contains a spring-loaded spool, wrapped with a nylon strap or tether that can be rendered locked in place by means of [a] an electronic braking device which is operated by a remote switch.

The nylon strap exits the housing and travels through the vehicle seat to the front. The spool is in its inactive mode, which allows the strap to be extracted freely. The police officer (operator) walks a handcuffed or similarly fettered prisoner to the front passenger door of his police vehicle. He then attaches the retractable nylon strap to the chain or other connector between the handcuffs by means of a clasp or other attachment mechanism. The suspect then sits down into the seat as the nylon strap self retracts into its housing through the seat. When the suspect is seated against the seatback, the operator may activate a remote-controlled switch, which may cause power, such as a 12-volt current, to engage the spool's braking mechanism and prevent the nylon strap from again being extracted. This action holds the prisoner's body and hands in place against the seat and prevents him/her from being able to move sufficiently enough to unlatch the seatbelt, unlock and open the door, or move their handcuffs to the front. This prevents their ability to assault the officer or operate the police vehicle.

By having the prisoner secured in such a manner, the police officer can then go about his other necessary duties which may include: dealing with other suspects, searching or inventorying a vehicle, talking with victims and witnesses. When a lone officer has more than one suspect, this device allows him the ability to secure multiple prisoners in his vehicle while preventing their ability to move sufficiently to physically interact with each other.

After concluding his on-scene duties, the officer is able to transport the prisoner from the scene to the police station or correctional facility for processing, knowing that the prisoner is secure and unable to make hazardous movements. After transport, the officer opens the prisoner's door and releases the electronic brake by means of the remote-controlled switch. The prisoner is directed to stand up and exit out of the vehicle. The officer can then unhook the nylon strap and escort the prisoner into the facility.

One major innovation of this invention is that it provides a retractable and locking device specifically designed to secure a handcuffed prisoner in place against a seat. This action prevents the prisoner from being able to move his hands and body sufficiently enough to release a seatbelt latch or unlock and open a door. This further prevents the prisoner from being able to move the handcuffs from back to front. The invention requires no major modification to the vehicle and it is relatively portable allowing for it to be removed and reinstalled into another vehicle.

Its design utilizes the installation behind the seat to combat the force that a prisoner could possibly exert in order to defeat the locked secure position of the nylon strap. As the prisoner pulls against the strap, it is additionally being reinforced by its position behind the seat.

Some additional advantages to the use of this invention are:

It causes minimal damage to a vehicle as a result of installation, and thus increases the vehicle resale value.

It can be easily moved from one vehicle and reinstalled into another.

It has a low profile design which allows the seat to still be utilized for non-prisoner passengers.

The low profile design and simplicity of use are less likely to create anxiety by the prisoner.

It provides an alternative to the use of a police cage.

In cases of emergency the transporting officer can release the prisoner by activating the remote switch. Additionally, the nylon strap can be cut with a knife or scissors to facilitate a quick release.

The brake for the spool containing the nylon strap is in a locked position when a 12-volt current is supplied to it by activation of the officer's remote-controlled switch. Should that current from the vehicle's battery be disrupted due to a collision, the brake may disengage and the strap may be extracted allowing for the prisoner to exit the vehicle.

The device is used in conjunction with the use of the vehicle's seatbelts. It does not interfere with the normal operation of a vehicle's seatbelt.

In accordance with another aspect of the invention, the retraction mechanism can be controlled by a remote control such as a wireless switch. The officer can activate the switch to lock or unlock the retraction mechanism remotely so that the police officer need not put his or her head or hands too close to the prisoner—thus minimizing the risk of an attack.

In accordance with another aspect of the invention, a visual indicator, such as a light may be mounted in or on the dashboard of the police car. The visual indicator confirms to the officer that the retraction mechanism remains locked, thereby assuring the officer that the prisoner is being held in the seat.

It is another object of the present invention to provide an improved prisoner safety seat. According to one aspect of the invention, the prisoner is provided a reasonably comfortable sitting position in a location so that the prisoner may be processed without risk to the officer. This could happen, for example, in a booking area. Likewise, a prisoner being treated at a medical facility can be retrained either before or during an appointment to reduce the risk of flight or an attack on medical personnel.

In accordance with another aspect of the invention, the prisoner safety seat is configured to that the prisoner is held in the safety seat or immediately adjacent thereto with either his or her hands behind the back or in front.

According to another aspect of the invention, the officer may remotely release the locking mechanism associated with the tether such that the prisoner may stand and/or even move away from the seat. This allows the officer more room to remove the tether and reduce the danger of close proximity to the prisoner and the chair, including any awkward positioning that may have been required.

These and other aspects of the present invention are realized in a prisoner safety seat as shown and described in the following figures and related description.

THE DRAWINGS

Various aspects of the present invention are illustrated in the accompanying drawings in which.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION OF THE INVENTION

Figure 1:
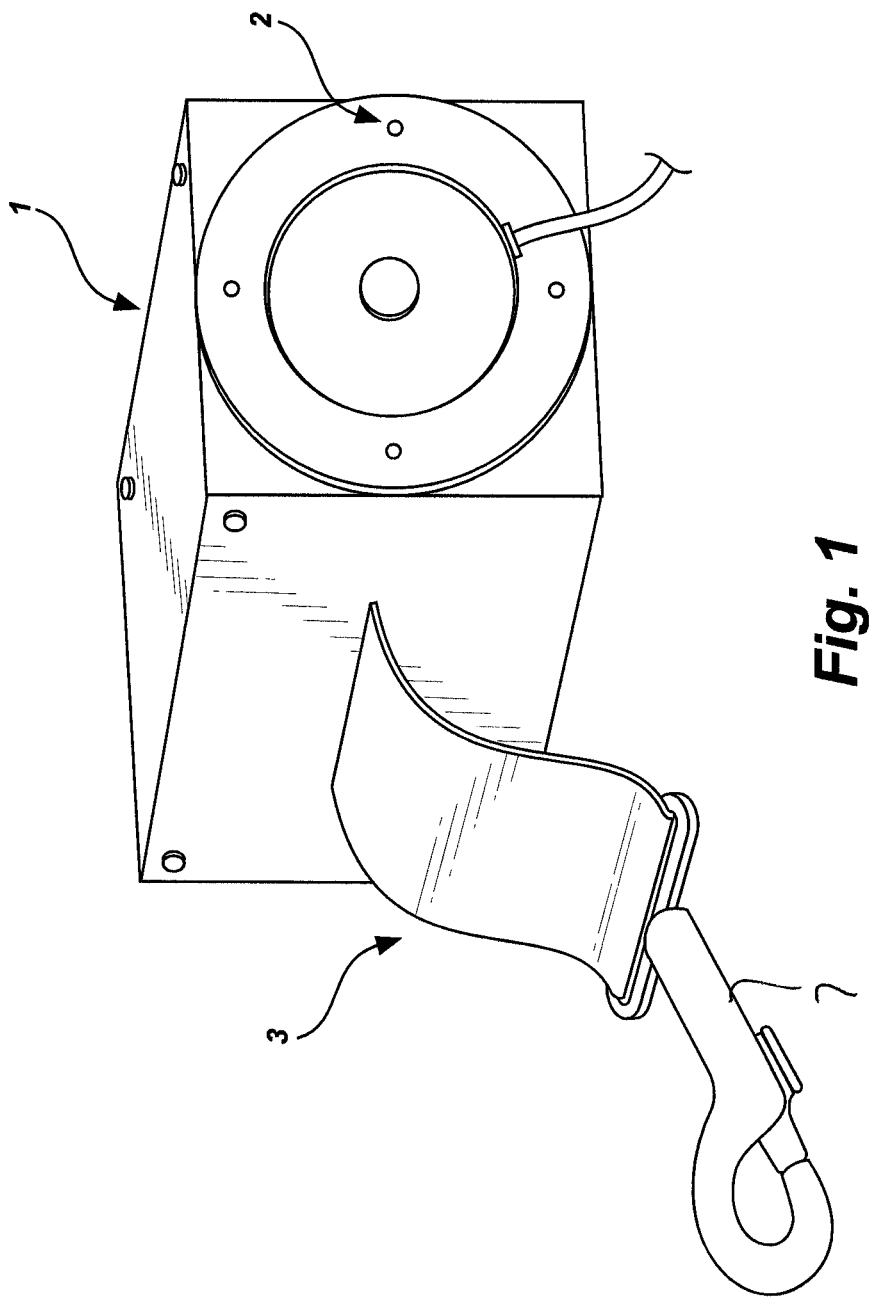
FIG. 1 is a view of the retractable restraint shown without a mounting system.

Turning to FIG. 1, there is shown a retractable restraint device, generally indicated at 1. The device includes a retraction assembly 2 and a tether or strap 3 which can be retracted into the retraction assembly and locked in place. An attachment mechanism 7, such as a clip or clasp can be disposed on the end of the strap 3 to clip onto a pair of handcuffs worn by a user.

Figure 2:
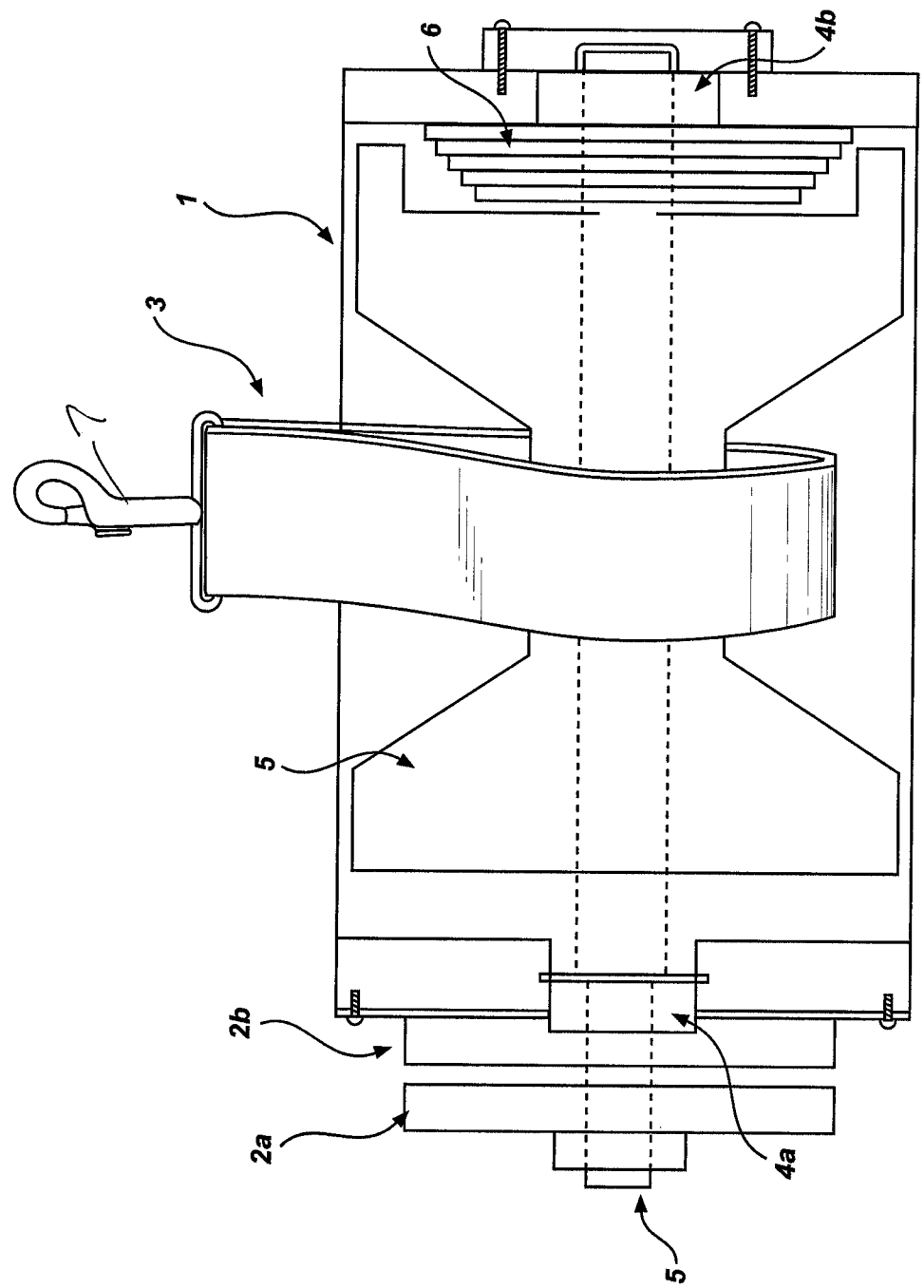
FIG. 2 is a cross section view of the retractable restraint showing the inner workings and components.

The retractable restraint device 1 as shown in FIG. 2 consists of the assembly 1; electromagnetic brake 2a, 2b); a tether or strap in the form of a strap assembly 3; sealed bearing assemblies 4a, 4b; shaft and spool assembly 5; return spring 6; and restraint strap 3.

The free end of the restraint strap 3 is allowed to pass from the assembly 1 through an opening cut into the assembly. The free end of the restraint strap 3 is intended to have a clasp, catch or hook 7 to attach to the restrained prisoner's handcuffs.

The restraint strap 3 is wound on the shaft and spool assembly 5 which is kept in a state of tension by return spring 6. This provides for the retraction of the restraint strap 3 when the invention is in the inactive mode. The shaft and spool assembly rides on the two bearing assemblies 4a, 4b to allow free movement of the shaft in either direction when the invention is in the inactive mode.

The electromagnetic brake assembly 2a, 2b may be a two-piece device consisting of an electromagnet 2b that is attached to the case assembly 1. The second part of the electromagnetic brake assembly 2a may be attached to the shaft with a set-screw and rotates with the shaft without interference from electromagnet 2b while the invention is in the inactive mode.

When voltage is applied (active mode) to the electromagnetic brake assembly 2a, 2b part 2b produces an electromagnetic force that pulls the friction material of electromagnetic brake assembly 2a into physical contact with electromagnetic brake assembly part 2b. This binds the electromagnetic brake assembly 2a which is attached to the shaft and spool assembly 5 to the electromagnetic brake assembly 2b which is attached to the case assembly 1. This renders the shaft and spool assembly 5 locked and immoveable preventing the strap assembly 3 from being pulled out of the case assembly 1.

Figure 3:
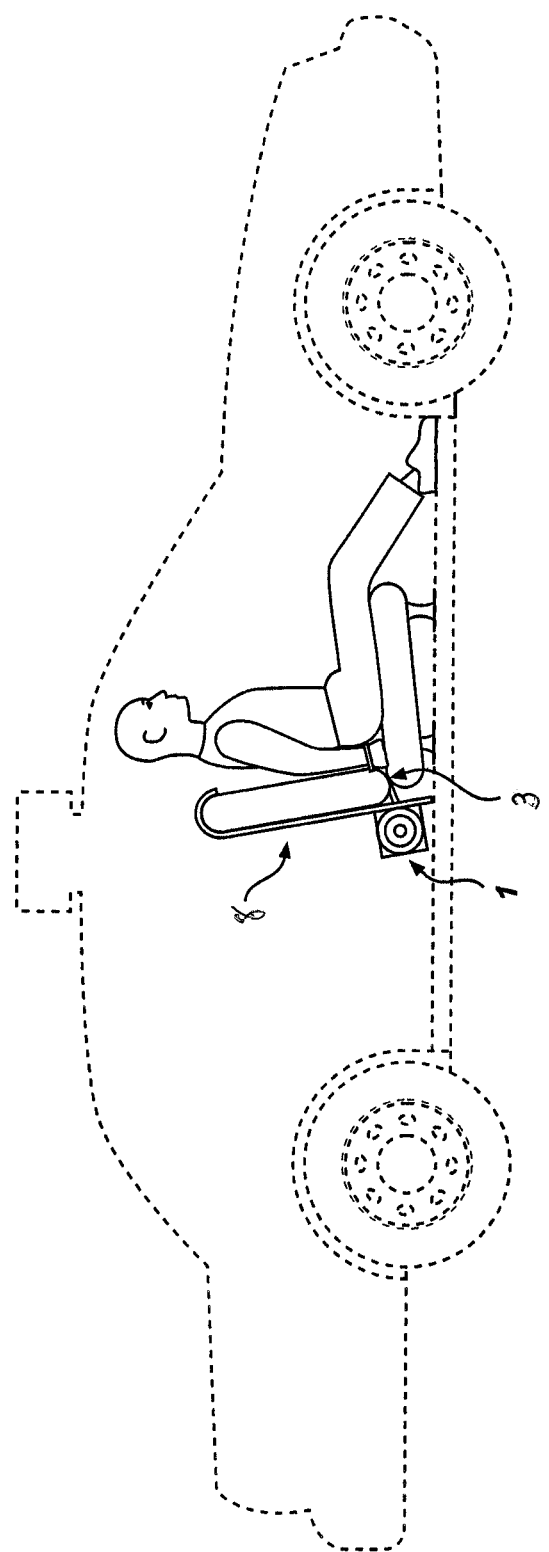
FIG. 3 is a side view of patrol car with the retractable restraint mounted to the backside of the front passenger seat. The restraint strap passes through the gap between the bottom of the seat and the seat back and attaches to the prisoner's handcuffs.

As shown in FIG. 3, the retractable restraint device 1 is disposed on a frame, indicated at 8, mounted to the backside of a seat such as the front passenger seat. The strap or tether 3 is passed through the gap between the seat back and the seat bottom and attached to the prisoner's handcuffs. In such a manner, the retractable restraint device holds the prisoner in the seat with his or her hands behind the prisoner, thereby substantially reducing the risk of an attack on the officer. When the officer reaches the desired destination, the officer can release the retractable restraint device 1 and allow the prisoner to get out of the car when the officer is ready and the prisoner is authorized to get out. Because the prisoner is still attached to the strap 3, the prisoner is unable to run until the officer removes the clasp 7 from the handcuffs. This provides the officer with substantially more control.

Figure 4:
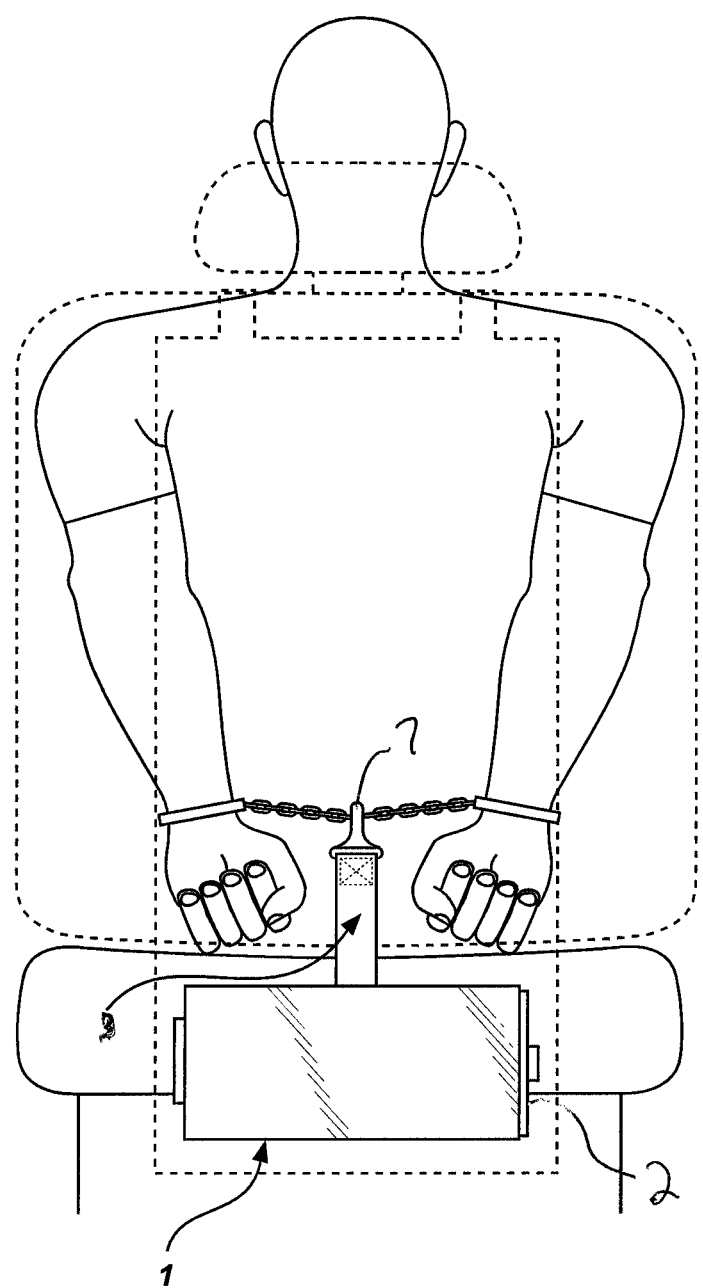
FIG. 4 is a rear view of the retractable restraint in use on the front passenger seat as shown in FIG. 3.

FIG. 4 shows the same example from a rear view.

When the retractable restraint device described in this invention is used to restrain a prisoner in the seat of a law enforcement vehicle, the following procedure would be followed. The prisoner would be escorted to the open door of the vehicle. The strap assembly 3 could either be simply lying on the seat and would need to be pulled out by the officer to hook to the handcuffs of the prisoner, or the strap assembly could be attached to the inside of the vehicle door with a hook-type device. This would allow the strap to be pulled out when opening the door allowing easy access. Since the invention is retractable, the strap would move in and out with the opening and closing of the door. In either case, the strap assembly would be attached to the handcuff of the prisoner, and the prisoner allowed to sit down in the seat. The retractable restraint 1 would retract the excess strap as the prisoner sits down. Once the prisoner is seated, the officer would activate the retractable restraint. (This could be accomplished in any number of ways, including RF remote control, other forms of wireless, a dash-mounted switch, or possibly a switch mounted on the rear of the device, out of the prisoner's reach.) Once the retractable restraint is activated, the electromagnetic brake would lock the shaft and spool assembly and the prisoner would be unable to exit the seat. Since, in most cases, the prisoner's knees would be higher in elevation than his hips, he would be at an anatomical disadvantage with respect to body leverage and would be less likely to overcome the strength of the electromagnetic brake assembly.

Upon arrival at a detention facility, the officer could remove the prisoner from the vehicle by deactivating the retractable restraint, thus freeing the shaft and spool assembly and allowing it to rotate freely. The prisoner could then exit the vehicle, pulling a length of strap assembly out as he/she stands up after receiving authorization. The strap assembly would then be allowed to either retract back into the device, or be attached to the door as outlined above, making it ready for the next use.

By default, the retractable restraint 1 is in an inactive state, meaning that as long as voltage is not applied to the electromagnetic brake assembly, the strap assembly is free to be pulled out of, or retract into, the device. This was a safety consideration in the design of the device. Since in the event of a mishap such as an accident, rollover or fire, power would most likely not be available to keep the device activated. A position sensor such as a mercury switch could be incorporated into the design to ensure that the device is only capable of being activated in an upright position.

The retractable restraint 1 could be used in a variety of different applications including, but not limited to, restraining a prisoner in a courtroom, the back seat of a vehicle, or used with K9 Units.

Figure 5:
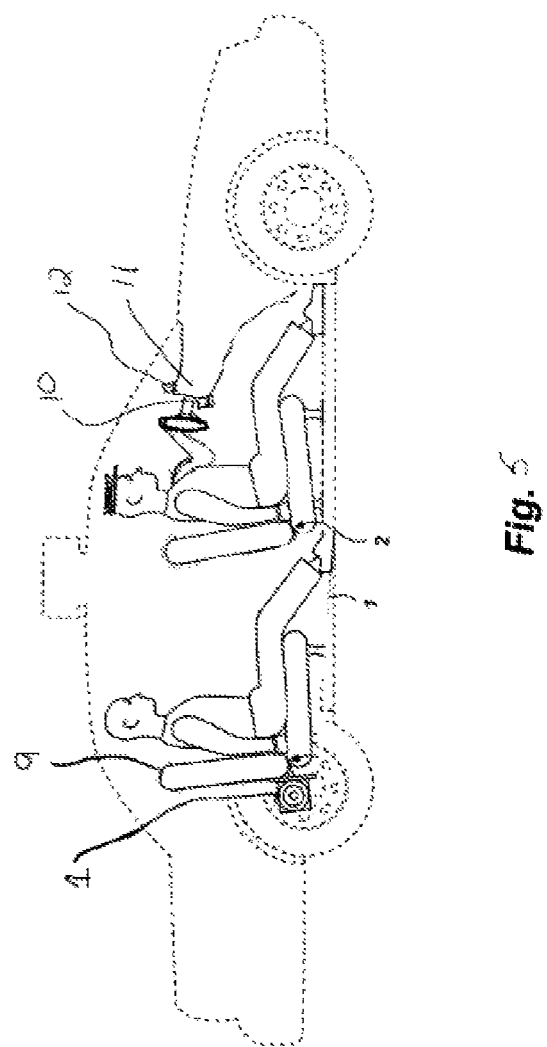
FIG. 5 is a side view of a patrol car with a retractable restraint in use in the rear seat, along with a wireless remote for selectively locking the retractable restraint, and a visual indicator of when the retractable restrain has been locked in a retracted position.

Turning now to FIG. 5, there is shown a side view of a police car similar to that of FIG. 3. Instead of the retractable restraint 1 being disposed on the back of the front seat, the device is disposed in the trunk so that the strap 3 extends between the upper and lower portions of the back seat 9. The retractable restraint 1 is activated by a remote control 10 which is preferably disposed away from the retractable restraint, such as on the dash board 11 or is a wireless remote which can be attached to the dash board or worn by the officer.

Also shown in FIG. 5 is a visual indicator 12 which can be mounted in or on the dash board. The visual indicator 12, such as a light, etc., gives of visual indication of whether or not the retractable restraint 1 is activated. As shown in FIG. 5, the retractable restraint 1 is disposed in the trunk of the vehicle and cannot be seen by the officer.

If the retractable restraint 1 is not active—due for example to the officer accidentally deactivating the locking mechanism via the remote control—the officer will be warned by the visual indicator 12 that the retractable restraint 1 is not active and that he or she needs to activate it to keep the prisoner held in the seat. The retractable restraint 1 could also be configured to sense if the prisoner has been able to remove the clasp 7 from the handcuffs, such as by determining tension on the strap.

In such a manner an officer is provided with a much safer method for transporting prisoners. The prisoner is under control as soon as the officer attaches the clasp 7 to his or her handcuffs and is maintained until the officer removes the clasp.

While an officer faces danger when moving a prisoner, some of the same concerns are also present when transferring or processing a prisoner, such as during booking. The officer must often enter information about the prisoner into a computer or other sort of logging system. During this time the officer may have his or her back turned to the prisoner. A prisoner could attack the officer or attempt to flee.

The safety chair can also be used in other contexts in which a prisoner might be restrained. For example, a potentially violent prisoner who needs medical treatment can be restrained prior to or even during the medical treatment. Likewise, a prisoner could be held prior to a court appearance, or even during trial if the prisoner poses an ongoing threat.

Figure 6:
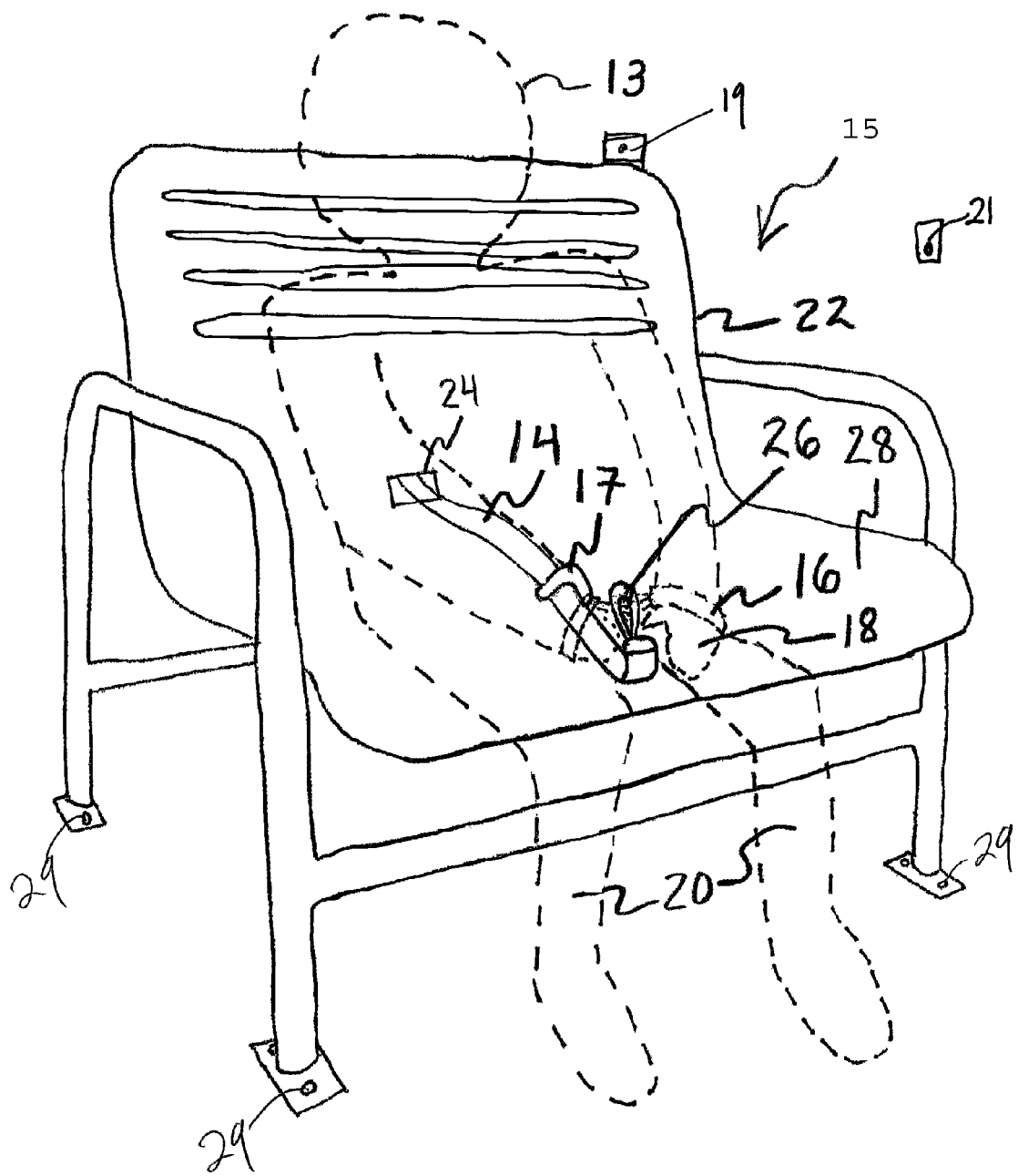
FIG. 6 shows a perspective view of an outline of a prisoner restrained with a safety seat device having a restraint device in accordance with the present invention.

Turning now to FIG. 6, a perspective view of an outline of a prisoner 13 restrained with a safety seat device 15 is shown. A tether or strap 14 may be extended such that it is attached to restraining device 16 on prisoner 13 while the prisoner is standing. As prisoner 13 sits down, tether or strap 14 may retract. Once retracted or during retraction, a locking mechanism similar to that discussed above or using some other form of brake or catch may be used to may ensure that tether 14 does not further extend.

As with the embodiment in the police car, the clasp 26 of the tether 14 may be attached to the handcuffs of a prisoner behind his or her back. As the prisoner sits and the tether 14 retracts, the prisoner is held in place while the officer handles the booking procedure. A visual indicator 19 could be used to show that the tether 14 is locked to hold the prisoner in place.

While prisoners often have their hands cuffed behind their backs, this is not always the case. Often the prisoner will have his or her hands cuffed together in front. To this end, one or more forward loops, rings or guides 17 may be provided on the safety seat device. In use, the tether 14 is passed through the guide(s) 17 and the clasp 26 is then attached to the handcuffs 16 worn by the prisoner. The guide moves the closest point of attachment for the tether 14 from the back portion of the safety seat device 15 to the front, adjacent to which the prisoner's handcuffs 26 will be located. The tether 14 can extend to the side of the prisoner, potentially allowing two different straps to be used on the same safety seat device 15 to hold two prisoners with their hands 18 adjacent the guide. In the alternative, the prisoner can be sat on the seat such that the guide 15 is disposed between his or her legs 20. In such a position, it is extremely difficult for the prisoner to even stand up without the tether 14 being released, let alone to assault the officer.

Once prisoner 13 is required to transfer from prisoner safety seat 15, the lock may be disengaged to allow tether 14 to extend. Prisoner 13 may then stand up and hold the prisoner's hands 18 forward to the officer. If safety dictates, the officer may re-engage the locking mechanism to prevent further forward movement by prisoner 13. The officer, if required, may then attach a new restraint before removing tether 14.

By having prisoner 13 move toward the officer and the officer be outside the tethered range, the officer remains dominant of the situation. The officer may be further protected because prisoner 13 may bring the prisoner's hands 18 to a position as directed by the officer rather than a position dictated by a mooring point. Finally, prisoner 13 may be moved sufficiently away from obstacles, such as a chair, that may be violently and quickly used against the officer. Moreover the safety seat 15 may include attachment mechanisms 29 so that it may be bolted or otherwise attached to the floor.

The retractable restraint (not shown except for strap 14 and clasp 26 in FIG. 6) may be remotely controlled by the officer. The remote control 21 of the locking mechanism may help ensure the safety of the officer such that the officer is not required to approach prisoner 13. Further, it may help the officer remain dominant during the transition.

The remote control 21 of the retractable restraint may be accomplished by many different technologies. The remote control may include wireless technologies, including but not limited to RF and IR, which may be based on digital or analog, such as WiFi. The remote control may include wired technologies, including a simple wired switch or a TCP/IP network interface.

Figure 7:
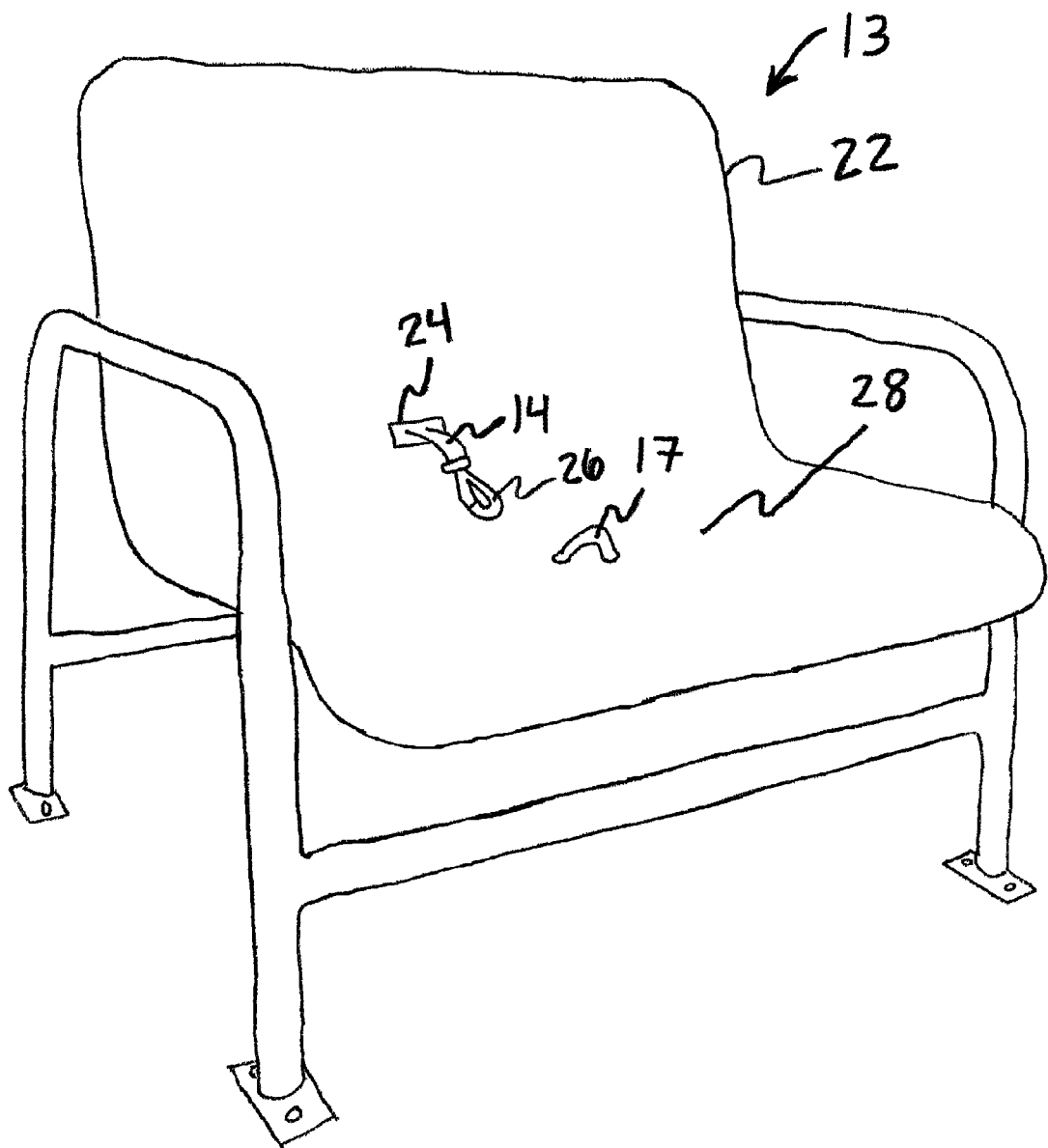
FIG. 7 shows a perspective view of a prisoner safety seat device.

Turning now to FIG. 7, a perspective view of a prisoner safety seat device 15 is shown. In one embodiment, a retractable restraint including the tether 14 and a locking mechanism (not shown) sit behind or under seat 22. Tether 14 is fed from the retraction mechanism through seat 22 by rear channel 24. The tether is then fed through the guide 17 which is disposed on the bottom portion of the seat 22. The guide 17 acts to restrict the movement of the prisoner is if the point of attachment will be any significant distance forward of the back portion of the seat 22. (It will be appreciated that multiple guides 17 may be provided to accommodate for prisoners of different sizes or to allow multiple prisoners on a bench, etc. Restraint attachment or clasp 26 may attach to a restraining device, such as handcuffs, which are already on the prisoner.

In another embodiment, the retraction mechanism may sit below the seat and feed the tether 14 through a channel in or on seat base 28. Instead of being pulled rearward, the prisoner's hands are pulled down toward seat base 28. As the prisoner's hands are pulled closer to seat base 28, the prisoner's hands movement, and correspondingly the prisoner's body movement, is restricted.

In another embodiment, the officer may choose to not use forward channel 17. The officer may attach tether 14 to a person handcuffed behind their back. By retracting tether 14 and activating the locking mechanism, a prisoner who is handcuffed behind their back may also be restrained.

Figure 8:
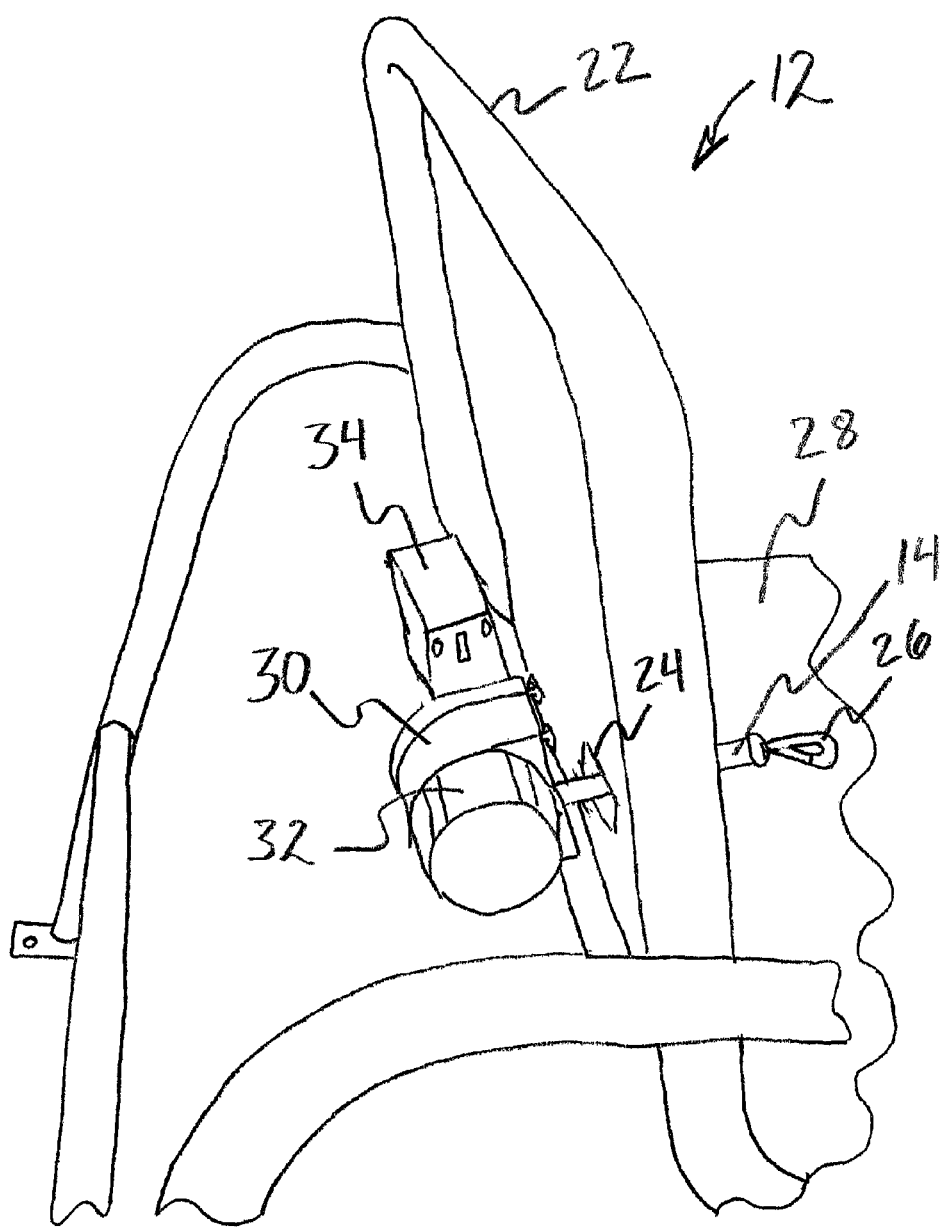
FIG. 8 shows a side view of a portion of a prisoner safety seat device.

Turning now to FIG. 8, a side view of a portion of a prisoner safety seat 12 is shown. In one embodiment, a retraction mechanism 30 and a locking mechanism 32 are mounted behind seat 22. Tether 14 is retracted or extended through rear channel 24. Tether 14 may be locked or freed by activating or disabling locking member 32.

Locking member 32 may be configured in several different ways. In one embodiment, locking member 32 may be configured to require an active signal or its status will change. For example, locking mechanism 32 may require that power be present or lock 32 would release. This release may be delayed and/or buffered by an external power source such as a battery or capacitor. This would give the advantage of releasing locking mechanism 32 in the event of a power failure. A wall plug may also be secured to an electrical source such that a prisoner could not pull or tamper with the electrical source and cause locking mechanism 32 to release.

Locking mechanism 32 may also be configured to retain its status until a different signal is received. In one embodiment, locking mechanism 32 may remain active until a disable signal is received. This may be advantageous because the officer may attend to other emergency situations occurring with a power failure without also attending to an unlocked tethered prisoner. Similarly, a prisoner tampering with or removing a plug to locking mechanism's 32 power source would still not be able to unlock the prisoner safety seat. A back-up battery or similar alternative power source may also provide power to change the state of the lock from activated to disabled in the event of a power loss.

The prisoner safety seat may also contain expansion module 34. In one embodiment, expansion module 34 may contain a battery which continues to provide locking member 32 and/or retraction mechanism 30 with extended power even during power loss. Having power available would allow an officer time to react to a situation involving power loss. It would also prevent damage to the prisoner safety seat 15 in the case where a prisoner had to be released during the power loss, but locking member 32 was configured to stay enabled in the event of a power loss.

In another embodiment, expansion module 34 may contain a network module. The network module may contain features that include wireless reporting wired reporting, remote network control, RFID or similar technology to give status of the prisoner and/or status or control of the prisoner safety seat.

The remote lock feature may be advantageous. In one embodiment, the prisoner may be remotely viewed through a window, CCTV or other remote viewing technology. Locking mechanism 32 may be remotely disabled through a network module version of the expansion module 34 and the prisoner ordered to stand up and move to a pre-determined position. Once at the pre-determined position, the officer may approach the prisoner and manually remove tether 14. In another embodiment, tether 14 may have an electromechanical release such that the officer is not required to approach the prisoner and release tether 14 from a restraining device on the prisoner.

Figure 9:
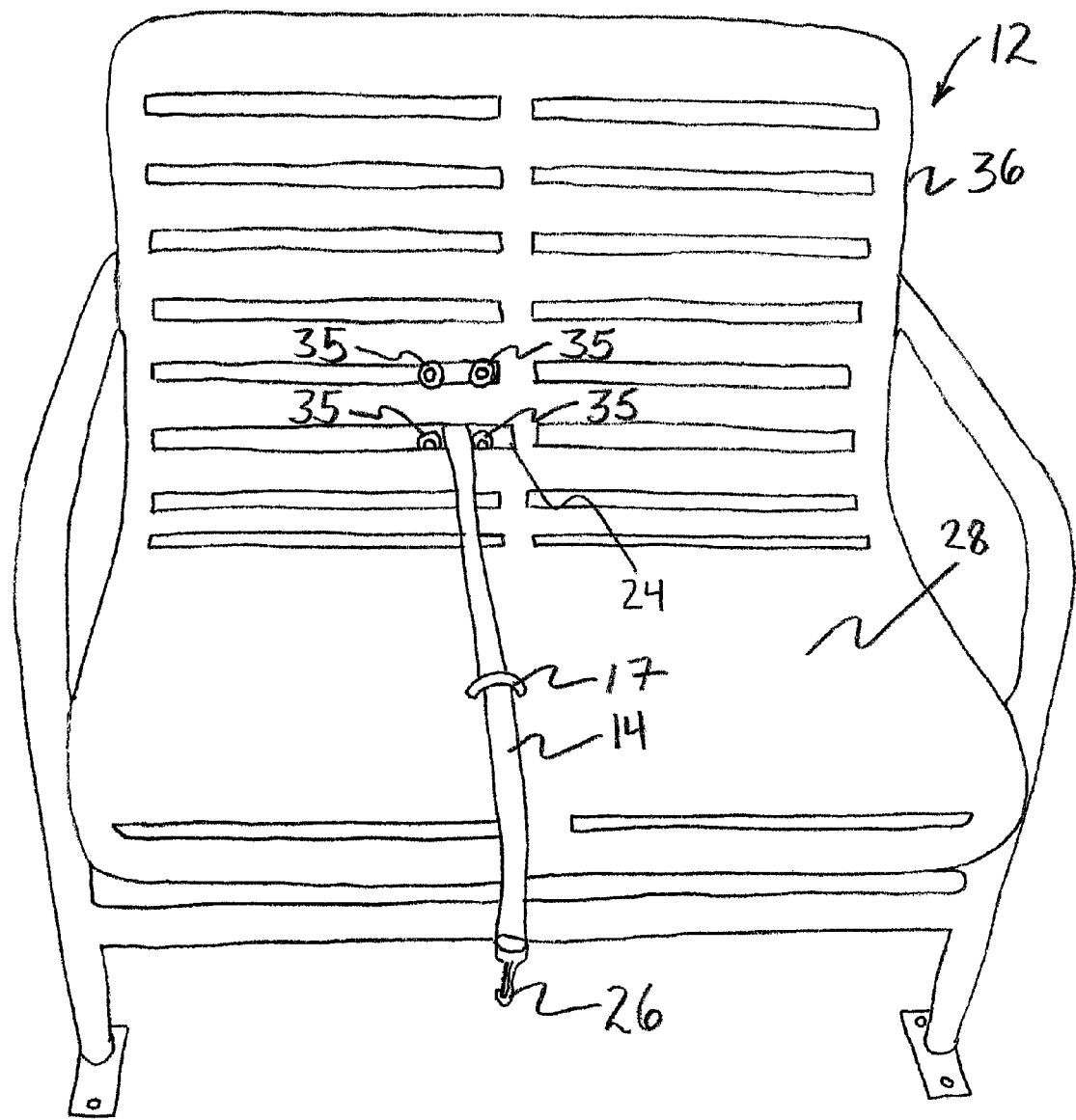
FIG. 9 shows a front view of a retro-fitted prisoner safety seat device.

Turning now to FIG. 9, a front view of a retro-fitted prisoner safety seat is shown. Prisoner safety seat technology may be fitted to existing chair 36 or benches in current facilities. In one embodiment, attachment points 35 may be bolted or welded to the existing chair 36. The retraction mechanism (see FIG. 8) and locking mechanism (see FIG. 8) may be affixed to these attachment points 35. If rear channel 24 does not already exist, it may be formed. Similarly, guide 17 may also be attached or formed. In some cases, guide 17 may be an arch of strong metal welded to seat base 28. This may be done in the middle of the chair 36 so that two prisoners could both be attached, or so that a single prisoner could be positioned with the guide 17 between his or her legs.

While the discussion may have centered on law enforcement and prisoners, it should be realized that there may be equal applicability to other areas, such as corrections use, military use and other areas where restraint may be used. Additionally, such a chair could be used in a courtroom with a dangerous prisoner. If the prisoner were placed in the seat with his or her hands placed in front or him/her, a jury would not see that the prisoner's hands are shackled and the prisoner is being restrained, while at the same time providing those in the court room a substantial improvement in safety.

There is thus disclosed an improved prisoner safety seat. It will be appreciated that numerous changes may be made to the present invention without departing from the scope of the claims.

What is claimed is:

1. A prisoner safety seat comprising:
    a seat having a seat base with an upper surface whereon a person sits, the seat base having a front and a back, the seat further comprising a channel adjacent the back of the seat base through which a retractable restraint extends;
    a retractable restraint device having a tether configured for attachment to attach to a pair of handcuffs, a retraction mechanism for retracting the tether and an electromagnetic locking mechanism for selectively limiting extension of the tether; and
    a guide formed along the upper surface of the seat base and configured to accept the retractable restraint such that a portion of the tether can be passed through the guide to restrain a person's hands; and
    wherein the retractable restraint has a first position wherein an end of the restraint is disposed adjacent the slot so as to hold a pair of handcuffs behind a person sitting on the seat base, and a second position, wherein the retractable restraint extends through the guide so as to hold handcuffs in front on a person sitting on the seat base, and a third position wherein the retractable restraint can be attached to handcuffs of a person standing in front of the seat base, and wherein the retractable restrain can be locked in the first or second position.

2. The prisoner safety seat of claim 1 further comprising a user activated control, remote from the electromagnetic locking mechanism and a person in the seat and configured for selectively locking the electromagnetic locking mechanism.

3. The prisoner safety seat of claim 2, wherein the seat comprises a channel formed therein for passing the tether through the seat, wherein the channel is disposed at or above the upper surface of the seat base, and wherein the electromagnetic locking mechanism engages only when a voltage is applied.

4. The prisoner safety of claim 3, wherein the seat has a back portion extending upwardly from the seat base, the upper surface of the seat base having rearward portion and a forward portion and wherein the channel is if formed in one of the rearward portion of the upper surface and the back portion such that a person sitting on the upper portion with hands handcuffed behind their back has their hands held adjacent the channel.

5. The prisoner safety seat of claim 1, further comprising an expansion module for communicating with remote devices and a battery contained within the expansion module.

6. The prisoner safety seat of claim 5, wherein the expansion module further comprises a network interface.

7. The prisoner safety seat of claim 1, wherein the seat has a back portion and a bottom portion and wherein the guide is disposed in the middle of the bottom portion such that a person could sit on either side of the guide or with the guide between their legs.

8. A prisoner safety seat comprising:
    a seat having a base portion with an upper surface on which a person sits;
    a tether configured to attach to a person;
    a retraction mechanism configured to retract the tether as the person sits on the upper surface, the retraction mechanism being mounted to the seat;
    a tether guide mounted upon the base portion of the seat and configured to accept the tether and restrain a person's hands;
    a locking mechanism configured to receive a signal and to prevent extension of the tether after receipt of the signal such that the tether is selectably lockable in a first position and a second position, the first position suitable for restraining the person's hands behind the person's back such that the person is held in the seat, the second position suitable for restraining the person's hands between the person's legs such that the person is held in the seat; and
    a user operated signal source remote to the person in the seat, the signal source providing the signal to the locking mechanism; and
    a visual indicator which identifies when the locking mechanism is activated; and
    wherein the base portion has a front edge and wherein the tether guide is attached to the base portion rearwardly of the front edge, and further comprising a position sensor configured to release a prisoner from the prisoner safety seat in the event that the prisoner safety seat is overturned.

9. The prisoner safety seat of claim 8, wherein the seat further comprises a tension sensor affixed to the locking mechanism and configured to determine whether the person is attached to the tether.

10. The prisoner safety seat of claim 8, wherein the tether has a length, the length being sufficient so that the person may exit a vehicle while the person's hands are attached to the tether.

11. A method for restraining a person in custody, the method comprising:
    selecting a seat having a base and a rear portion and a tether connected to an electromagnetic retraction mechanism, the tether having an attachment mechanism on a free end thereof and extending through a channel adjacent the rear portion of the seat;
    selectively placing the tether through a guide located on the base portion of the seat and attaching the attachment mechanism to a pair of handcuffs on the person when it is desired to restrain the person with handcuffs in front of the person and attaching the attachment mechanism to handcuffs on the person without passing through the guide when it is desired to restrain the person with handcuffs behind the person;
    retracting the tether as the person sits in the seat; and
    locking the electromagnetic retraction mechanism such that the tether cannot be extended, to hold the person in the seat by use of a control operated by a second person.

12. The method according to claim 11, wherein the method comprises using a seat having the electromagnetic retraction mechanism disposed on an opposite side of the seat than the person wearing the restraint mechanism.

13. The method according to claim 11, wherein the method further comprises: locking the electromagnetic retraction mechanism when voltage is applied; and producing a visual indication when the electromagnetic retraction mechanism is locked to thereby ensure that the person is properly restrained in the seat.

14. The method according to claim 11, wherein the method comprises sitting the person wearing a restraint mechanism into the seat so that the guide is disposed between the person's legs.

15. The method according to claim 11, wherein the method comprises using a wireless remote to unlock the retraction mechanism.

16. The method according to claim 11, further comprising: providing information about whether the electromagnetic retraction mechanism is locked over a network; determining a tension in the tether; and providing information over a network about whether a person is attached to the tether.

* * * * *